United States Patent [19]
Mito

[11] Patent Number: 6,040,270
[45] Date of Patent: Mar. 21, 2000

[54] HERBICIDAL COMPOSITION

[75] Inventor: Nobuaki Mito, Kobe, Japan

[73] Assignee: Sumitomo Chemical Company, Limited, Osaka-fu, Japan

[21] Appl. No.: 09/147,960

[22] PCT Filed: Feb. 13, 1998

[86] PCT No.: PCT/JP98/00578

§ 371 Date: Mar. 24, 1999

§ 102(e) Date: Mar. 24, 1999

[87] PCT Pub. No.: WO98/35558

PCT Pub. Date: Aug. 20, 1998

[30] Foreign Application Priority Data

| Feb. 17, 1997 | [JP] | Japan | 9-032398 |
| Feb. 17, 1997 | [JP] | Japan | 9-032399 |
| Feb. 17, 1997 | [JP] | Japan | 9-032400 |
| Feb. 17, 1997 | [JP] | Japan | 9-032405 |

[51] Int. Cl.[7] ............... A01N 43/58; A01N 57/02
[52] U.S. Cl. ................................................. 504/128
[58] Field of Search ................................. 504/128

[56] References Cited

FOREIGN PATENT DOCUMENTS

WO 96/39392   12/1996   WIPO.
97/07104       2/1997   WIPO ............... A01N 43/58

*Primary Examiner*—S. Mark Clardy
*Attorney, Agent, or Firm*—Sughrue, Mion, Zinn, Macpeak & Seas, PLLC

[57] ABSTRACT

A herbicidal composition for foliar treatment is described, which contains as active ingredients, (a) a compound of general formula [1] wherein R is alkyl, cycloalkyl, alkenyl, dimethylamino, or diethylamino; and (b) glyphosate or a salt thereof, or glufosinate-ammonium. The herbicidal composition is useful for effective control of a wide variety of weeds in upland fields, particularly in corn fields and in soybean fields. Also described are a weeding method by foliar treatment of weeds with the above herbicidal composition; and use as a herbicide for foliar treatment, of a mixture of the above active ingredients.

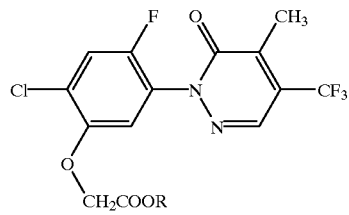

[1]

51 Claims, No Drawings

HERBICIDAL COMPOSITION

This application has been filed under 35 USC 371 as the national stage of international application PCT/JP98/00578, filed Feb. 13, 1998.

TECHNICAL FIELD

The present invention relates to a herbicidal composition, and more particularly, it relates to a herbicidal composition for foliar treatment and a weeding method by foliar treatment of weeds therewith.

BACKGROUND ART

At the present time, numerous herbicides are commercially available and they are widely used. There are, however, many species of weeds to be controlled and their growth extends over a long time. For this reason, requested are herbicides with higher herbicidal activity, wide herbicidal spectrum, and safety to crops.

DISCLOSURE OF THE INVENTION

The present inventor has intensively studied to find out excellent herbicides. As a result, he has found that various weeds growing in crop lands or non-crop lands can be effectively controlled by foliar treatment of these weeds with a herbicidal composition containing as active ingredients, (a) a compound of the general formula:

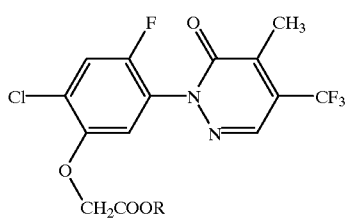

[1]

wherein R is $C_1$–$C_7$ alkyl, $C_5$–$C_6$ cycloalkyl, $C_2$–$C_6$ alkenyl, dimethylamino, or diethyl-amino; and (b) N-(phosphonomethyl)glycine (common name, glyphosate; hereinafter referred to as glyphosate) or a salt thereof, or ammonium DL-homoalanin-4-yl-(methyl) phosphinate (common name, glufosinate-ammonium; hereinafter referred to as glufosinate-ammonium). He has further found that the herbicidal activity is synergistically increased as compared with the cases where the active ingredients are independently used, and the herbicidal composition can, therefore, be applied at a lower amount; and that the herbicidal spectrum is expanded and a wide variety of weeds can be selectively controlled, particularly in corn fields and in soybean fields, thereby completing the present invention.

Thus, the present invention provides a herbicidal composition for foliar treatment comprising as active ingredients, (a) a compound of general formula [1] as depicted above, and (b) glyphosate or a salt thereof, or glufosinate-ammonium (hereinafter referred to as the present composition); and a weeding method by foliar treatment of weeds therewith.

MODE FOR CARRYING OUT THE INVENTION

Compound [1], one of the active ingredients of the present composition, can be produced by the methods as described in the following production examples.

PRODUCTION EXAMPLE 1

To a solution of 5.3 g (53.3 mmol) of sodium acetate mixed with about 100 ml of water was added under ice cooling 6.6 g (24.3 mmol) of 1,1-dibromo-3,3,3-trifluoroacetone, and the mixture was stirred at 70° C. for 20 minutes. The reaction mixture was cooled to room temperature, to which a solution of 5.8 g (21.5 mmol) of 2-fluoro-4-chloro-5-isopropoxyphenylhydrazine dissolved in about 20 ml of diethyl ether was added, and the mixture was stirred at room temperature for 1 hour. The ether layer was separated and then concentrated. About 60 ml of tetrahydrofuran (hereinafter referred to as THF) was added to the residue, to which 8.3 g (23.0 mmol) of (carbethoxyethylidene)triphenylphosphorane was added, and the mixture was heated under reflux for 2 hours. The THF was distilled out under reduced pressure, and the residue was subjected to silica gel column chromatography, which afforded 3.8 g (10.5 mmol) of 2-[2-fluoro-4-chloro-5-isopropoxyphenyl]-4-methyl-5-trifluoromethylpyridazin-3-one.

Then, 3.5 g (9.7 mmol) of 2-[2-fluoro-4-chloro-5-isopropoxyphenyl]-4-methyl-5-trifluoromethylpyridazin-3-one was dissolved in about 10 ml of concentrated sulfuric acid under ice cooling, and the solution was warmed to room temperature. After ten minutes, about 100 ml of water was added to the reaction mixture. The deposited crystals were collected by filtration, and then washed twice with 20 ml of water and once with 10 ml of hexane in this order. The crystals thus obtained were recrystallized from isopropanol, which afforded 3.2 g (9.9 mmol) of 2-[2-fluoro-4-chloro-5-hydroxyphenyl]-4-methyl-5-trifluoromethylpyridazin-3-one.

Then, 3.2 g (9.9 mmol) of 2-[2-fluoro-4-chloro-5-hydroxyphenyl]-4-methyl-5-trifluoromethylpyridazin-3-one was dissolved in about 50 ml of N,N-dimethylformamide, to which 0.44 g (11 mmol) of sodium hydride (60 wt % oil dispersion) was added at room temperature. The mixture was left stand at room temperature for 30 minutes and then cooled with ice, to which 1.8 g (11 mmol) of ethyl bromoacetate was added. The mixture was stirred at room temperature for 1 hour, to which diethyl ether and water were added in this order to make an extraction. The organic layer was washed with 10% aqueous hydrochloric acid solution, saturated aqueous sodium hydrogencarbonate solution, and saturated aqueous sodium chloride solution in this order, and then dried over anhydrous magnesium sulfate. The solvent was distilled out under reduced pressure, and the residue was subjected to silica gel column chromatography, which afforded 2.4 g (5.5 mmol) of ethyl 2-chloro-4-fluoro-5-(4-methyl-5-trifluoromethyl-3-pyridazinon-2-yl)phenoxyacetate (compound [1] wherein R is ethyl; hereinafter referred to as compound A), m.p., 102.0° C.

PRODUCTION EXAMPLE 2

The same procedure as described in Production Example 1 is repeated, except that the following reaction reagents are substituted for ethyl bromoacetate. Thus, the desired ester derivatives of 2-chloro-4-fluoro-5-(4-methyl-5-trifluoromethyl-3-pyridazinon-2-yl)phenoxyacetic acid can be obtained.

TABLE 1

| Reaction reagent* | Ester produced* | Compound symbol | Physical property (m.p.) |
|---|---|---|---|
| Methyl bromoacetate | Methyl ester | B | 80.4° C. |
| Ptopyl bromoacetate | Propyl ester | C | 82.9° C. |
| Butyl bromoacetate | Butyl ester | D | 75.6° C. |
| Pentyl chloroacetate | Pentyl ester | E | |
| Hexyl bromoacetate | Hexyl ester | F | |
| Heptyl bromoacetate | Heptyl ester | G | 63.2° C. |
| i-Propyl bromoacetate | i-Propyl ester | H | |
| i-Butyl bromoacetate | i-Butyl ester | I | |
| t-Butyl bromoacetate | t-Butyl ester | J | |
| c-Pentyl bromoacetate | c-Pentyl ester | K | |
| c-Hexyl bromoacetate | c-Hexyl ester | L | |
| Allyl bromoacetate | Allyl ester | M | |
| Vinyl chloroacetate | Vinyl ester | N | |

*: "i-", "t-", and "c-" mean iso-, tertiary-, and cyclo-, respectively.

$^1$H-NMR (250 MHz or 300 MHz, CDCl$_3$, TMS, δ (ppm))

Compound E 0.88 (3H, t, J=7 Hz), 1.2–1.4 (4H, m), 1.55–1.70 (2H, m), 2.43 (3H, q, J=2Hz), 4.19 (2H, t, J=7 Hz), 4.68 (2H, s), 6.98 (1H, d, J=7 Hz), 7.33 (1H, d, J =8Hz) 7.99 (1H, s)

Compound H 1.26 (6H, d, J=6.3 Hz), 2.43 (3H, q, J=2 Hz), 4.65 (2H, s), 5.05–5.18 (1H, m), 6.98 (1H, d, J=7 Hz), 7.33 (1H, d, J=8 Hz), 7.98 (1H, s)

Compound I 0.90 (6H, d, J=6.6 Hz), 1.85–2.03 (1H, m), 2.42 (3H, q, J=1.8 Hz), 3.98 (2H, d, J=6.5 Hz), 4.70 (2H, s), 6.99 (1H, d, J=6.3 Hz), 7.33 (1H, d, J=9.1 Hz), (1H, s)

Compound J 1.45–1.53 (9H, m), 2.39–2.45 (3H, m), 4.58–4.60 (2H, m), 6.96–7.00 (1H, m), 7.30–7.36 (1H, m), 7.96–8.00 (1H, m)

Compound K 1.5–1.9 (8H, m), 2.43 (3H, q, J=2 Hz), 4.65 (2H, s), 5.2–5.4 (1H, m), 6.97 (1H, d, J=7 Hz), 7.33 (1H, d, J=8 Hz), 7.98 (1H, s)

Compound M 2.42 (3H, q, J=1.9 Hz), 4.67–4.72 (2H, m), 5.23–5.37 (2H, m), 5.84–5.98 (1H, m), 7.00 (1H, d, J=6.3 Hz), 7.33 (1H, d, J=9.2 Hz), 7.99 (1H, s)

Compound N 2.42 (3H, q, J=1.8 Hz), 4.68–4.71 (1H, m), 4.77 (2H, s), 4.94–5.01 (1H, m), 7.03 (1H, d, J=6.3 Hz), 7.26–7.31 (1H, m), 7.34 (1H, d, J=9.0 Hz), 7.99 (1H, s)

PRODUCTION EXAMPLE 3

First, 1.0 g of the above compound A was dissolved in 15 ml of 1,4-dioxane, to which 15 ml of concentrated hydrochloric acid was added. This solution was warmed to 60° C., stirred for 6 hours, and then extracted with ethyl acetate. The organic layer was washed with aqueous sodium hydrogencarbonate solution and saturated aqueous sodium chloride solution in this order, and then dried over anhydrous magnesium sulfate. The solvent was distilled out under reduced pressure. The residue was dissolved in 5 g of thionyl chloride, heated under reflux for 1 hour, and then concentrated under reduced pressure. The residue was dissolved in 20 ml of THF at room temperature, to which 0.65 g of N,N-diethylhydroxylamine was added dropwise, and the mixture was then concentrated under reduced pressure. The residue was subjected to silica gel column chromatography, which afforded 1.1 g of O-[2-chloro-4-fluoro-5-(4-methyl-5-trifluoromethyl-3-pyridazinon-2-yl)phenoxyacetyl]-N,N-diethylhydroxylamine (compound [1] wherein R is diethylamino; hereinafter referred to as compound O).

[1] H-NMR (250 MHz, CDCl$_3$, TMS, δ (ppm)) 1.10 (6H, t, J=7.1 Hz), 2.42 (3H, q, J=1.9 Hz), 2.94 (4H, q, J=7.1 Hz), 4.74 (2H, s), 7.01 (1H, d, J=6.3 Hz) 7.33 (1H, d, J=9.1 Hz), 7.97 (1H, s)

PRODUCTION EXAMPLE 4

The same procedure as described in Production Example 3 is repeated, except that N,N-dimethylhydroxylamine is substituted for N,N-diethylhydroxylamine. Thus, O-[2-chloro-4-fluoro-5-(4-methyl-5-trifluoromethyl-3-pyridazinon-2-yl)phenoxyacetyl]-N,N-dimethylhydroxylamine (compound [1] wherein R is dimethylamino; hereinafter referred to as compound P) can be obtained.

Glyphosate and glufosinate-ammonium are compounds as described in Farm Chemicals Handbook, 1995 (published by Meister, Publishing Co., 1995), page C188. In the present invention, salts mean all agrochemically acceptable salts.

The present invention provides a herbicidal composition that is effective for control of a wide variety of weeds with crop selectivity, in particular for application to a new cultivation method such as non-tillage cultivation in corn fields and in soybean fields, and for control of a wide variety of weeds, which will grow over a period of winter to spring, before sowing of crops, while it causes no significant phytotoxicity on crops such as corn and soybean, which have been sowed after the application.

The present composition wherein component (b) is glyphosate or a salt thereof can effectively control unfavorable other plants in the case where cultivated are crops with resistance by introducing thereinto a herbicide resistance gene as described in the publications, e.g., the published specification of International Patent Application WO92/04449, and U.S. Pat. Nos. 5,510,471 and 5,633,448, while it causes no significant phytotoxicity on such crops.

The present composition wherein component (b) is glufosinate-ammonium can effectively control unfavorable other plants in the case where cultivated are crops with resistance by introducing thereinto a herbicide resistance gene as described in the publications, e.g., the published specification of International Patent Application WO87/05629, while it causes no significant phytotoxicity on such crops.

The present invention provides a herbicidal composition that is effective for control of a wide variety of weeds in non-crop lands. The herbicidal composition of the present invention effectively controls the main weeds in corn fields and in soybean fields, e.g., dicotyledonous plants such as wild buckwheat (*Polygonum convolvulus*), pale smartweed (*Polygonum lapathifolium*), pennsylvania smartweed (*Polygonum pensylvanicum*), common purslane (*Portulaca oleracea*), common lambsquarters (*Chenopodium album*), redroot pigweed (*Amaranthus retroflexus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), ivyleaf morningglory (*Ipomoea hederacea*), tall morningglory (*Ipomoea purpurea*), entireleaf morningglory (*Ipomoea hederacea* var. *integriuscula*), jimsonweed (*Datura stramonium*), black nightshade (*Solanum nigrum*), common cocklebur (*Xanthium strumarium*), common sunflower (*Helianthus annuus*), field bindweed (*Convolvulus arvensis*), sun spurge (*Euphorbia helioscopia*), devils beggarticks (*Bidens frondosa*), and common ragweed (*Ambrosia artemisiifolia*); and monocotyledonous plants such as barnyardgrass (*Echinochloa crusgalli*), green foxtail (*Setaria viridis*), giant foxtail (*Setaria*

*faberi*), yellow foxtail (*Setaria glauca*), southern crabgrass (*Digitaria ciliaris*), goosegrass (*Eleusine indica*), johnsongrass (*Sorghum halepense*), quackgrass (*Agropyron repens*), and shattercane (*Sorghum bicolor*), while it exhibits no significant phytotoxicity on crops such as corn and soybean.

In the present composition, the mixing ratio of component (a) to component (b), although it may vary with the species of weeds to be controlled, situation and conditions of application, and other factors, is as follows:

The weight ratio of compound [1] to glyphosate or a salt thereof is usually in the range of 1:5 to 500.

The weight ratio of compound [1] to glufosinate-ammonium is usually in the range of 1:2 to 200.

The present composition may be usually used in the form of formulations such as emulsifiable concentrates, wettable powders, or flowables, which can be prepared by mixing the composition with solid carriers, liquid carriers, or other bulking agents, and if necessary, adding surfactants or other adjuvants to this mixture. In such a formulation, component (a) and component (b) are usually contained at the total amount of 0.5 to 90 wt %, preferably 1 to 80 wt %.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfate esters; alkylsulfonate salts; alkylarylsulfonate salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., powdered starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present composition can also be prepared by making the active ingredients into the respective formulations using the above formulation technique and then mixing these formulations.

The present composition thus formulated may be applied to plants as such, or after diluted with water or other solvents. The present composition may also be used in admixture with other herbicides, in which case the herbicidal activity can be expected to be enhanced. The present composition can also be used together with insecticides, bactericides, fungicides, plant growth regulators, fertilizers, soil conditioners, or other agents.

The application amount of the present composition, although it may vary with the mixing ratio of component (a) to component (b) as the active ingredient compounds, weather conditions, formulation types, application times, application methods, application places, weeds to be controlled, and crops to be protected, is usually in the range of 10 to 8000 g, preferably 10 to 2000 g, as the total amount of active ingredient compounds per hectare. In the case of emulsifiable concentrates, wettable powders, flowables, or other similar formulations, they are usually applied after diluted in their prescribed amounts with water at a ratio of 100 to 1000 liters per hectare.

The following will describe formulation examples, in which parts are by weight.

FORMULATION EXAMPLE 1

One part of compound A, B, C, D, E, F, G, H, I, J, K, L, M, N, O, or P, 50 parts of glyphosate or a salt thereof, 3 parts of calcium lignin sulfonate, 2 parts of sodium laurylsulfate, and 44 parts of synthetic hydrated silicon oxide are well pulverized and mixed to give a wettable powder for each compound.

FORMULATION EXAMPLE 2

One part of compound A, B, C, D, E, F, G, H, I, J, K, L, M, N, O, or P, 25 parts of glyphosate or a salt thereof, 3 parts of calcium lignin sulfonate, 2 parts of sodium laurylsulfate, and 69 parts of synthetic hydrated silicon oxide are well pulverized and mixed to give a wettable powder for each compound.

FORMULATION EXAMPLE 3

Ten parts of compound A, B, C, D, E, F, G, H, I, J, K, L, M, N, O, or P, 65 parts of glyphosate or a salt thereof, 3 parts of calcium lignin sulfonate, 2 parts of sodium laurylsulfate, and 20 parts of synthetic hydrated silicon oxide are well pulverized and mixed to give a wettable powder for each compound.

FORMULATION EXAMPLE 4

One part of compound A, B, C, D, E, F, G, H, I, J, K, L, M, N, O, or P, 25 parts of glyphosate or a salt thereof, 3 parts of polyoxyethylene sorbitan monooleate, 3 parts of CMC (carboxymethylcellulose), and 68 parts of water are mixed and wet pulverized until the particle size comes to 5 microns or smaller to give a flowable for each compound.

FORMULATION EXAMPLE 5

A half part of compound A, B, C, D, E, F, G, H, I, J, K, L, M, N, O, or P, 25 parts of glyphosate or a salt thereof, 3 parts of polyoxyethylene sorbitan monooleate, 3 parts of CMC (carboxymethylcellulose), and 68.5 parts of water are mixed and wet pulverized until the particle size comes to 5 microns or smaller to give a flowable for each compound.

FORMULATION EXAMPLE 6

Two and a half parts of compound A, B, C, D, E, F, G, H, I, J, K, L, M, N, O, or P, 25 parts of glyphosate or a salt thereof, 3 parts of polyoxyethylene sorbitan monooleate, 3 parts of CMC (carboxymethylcellulose), and 66.5 parts of water are mixed and wet pulverized until the particle size comes to 5 microns or smaller to give a flowable for each compound.

FORMULATION EXAMPLE 7

Two parts of compound A, B, C, D, E, F, G, H, I, J, K, L, M, N, O, or P, 50 parts of glufosinate-ammonium, 3 parts of calcium lignin sulfonate, 2 parts of sodium laurylsulfate, and 43 parts of synthetic hydrated silicon oxide are well pulverized and mixed to give a wettable powder for each compound.

FORMULATION EXAMPLE 8

One part of compound A, B, C, D, E, F, G, H, I, J, K, L, M, N, O, or P, 25 parts of glufosinate-ammonium, 3 parts of calcium lignin sulfonate, 2 parts of sodium laurylsulfate, and 69 parts of synthetic hydrated silicon oxide are well pulverized and mixed to give a wettable powder for each compound.

FORMULATION EXAMPLE 9

Ten parts of compound A, B, C, D, E, F, G, H, I, J, K, L, M, N, O, or P, 50 parts of glufosinate-ammonium, 3 parts of calcium lignin sulfonate, 2 parts of sodium laurylsulfate, and 35 parts of synthetic hydrated silicon oxide are well pulverized and mixed to give a wettable powder for each compound.

FORMULATION EXAMPLE 10

Twenty-five parts of compound A, B, C, D, E, F, G, H, I, J, K, L, M, N, O, or P, 50 parts of glufosinate-ammonium, 3 parts of calcium lignin sulfonate, 2 parts of sodium laurylsulfate, and 20 parts of synthetic hydrated silicon oxide are well pulverized and mixed to give a wettable powder for each compound.

FORMULATION EXAMPLE 11

One part of compound A, B, C, D, E, F, G, H, I, J, K, L, M, N, O, or P, 25 parts of glufosinate-ammonium, 3 parts of polyoxyethylene sorbitan monooleate, 3 parts of CMC (carboxymethylcellulose), and 68 parts of water are mixed and wet pulverized until the particle size comes to 5 microns or smaller to give a flowable for each compound.

FORMULATION EXAMPLE 12

Two parts of compound A, B, C, D, E, F, G, H, I, J, K, L, M, N, O, or P, 25 parts of glufosinate-ammonium, 3 parts of polyoxyethylene sorbitan monooleate, 3 parts of CMC (carboxymethylcellulose), and 67 parts of water are mixed and wet pulverized until the particle size comes to 5 microns or smaller to give a flowable for each compound.

FORMULATION EXAMPLE 13

One part of compound A, B, C, D, E, F, G, H, I, J. K, L, M, N, O, or P, 40 parts of glufosinate-ammonium, 3 parts of polyoxyethylene sorbitan monooleate, 3 parts of CMC (carboxymethylcellulose), and 53 parts of water are mixed and wet pulverized until the particle size comes to 5 microns or smaller to give a flowable for each compound.

The following will describe test examples.
Evaluation Criteria

The herbicidal activity is evaluated at 11 levels with indices of 0 to 10, i.e., shown by numeral "0", "1", "2", "3", "4","5", "6", "7", "8", "9", or "10", wherein "0" means that there was no or little difference in the degree of germination or growth between the treated plants and the untreated plants at the time of examination, and "10" means that the test plants died completely or their germination or growth was completely inhibited. The herbicidal activity is excellent when ranked at "7", "8", "9", or "10", but insufficient when ranked at "6" or lower. The phytotoxicity is shown by "no injury" when no significant phytotoxicity was observed; "low" when low phytotoxicity was observed; "moderate" when moderate phytotoxicity was observed; or "high" when high phytotoxicity was observed.

TEST EXAMPLE 1

Cylindrical plastic pots each having a diameter of 17 cm and a depth of 14.5 cm were filled with upland soil, and then seeded with giant foxtail (*Setaria faberi*), barnyardgrass (*Echinochloa crus-galli*), and annual bluegrass (*Poa annua*). These test plants were grown in a greenhouse: giant foxtail for 42 days, and barnyardgrass and annual bluegrass for 31 days.

An emulsifiable concentrate of compound A, which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexanone, a formulation product of glyphosate (trade name, Roundup; seller, Monsant Japan Limited; distributor, Sankyo Co., Ltd.), and a mixture of the emulsifiable concentrate of compound A and the formulation product of glyphosate were independently diluted in their prescribed amounts with water. Each dilution was uniformly sprayed over the test plants with a small sprayer. After the application, the test plants were grown in the greenhouse for 4 days, and the herbicidal activity was then examined.

The results are shown in Table 2.

TABLE 2

| | | Herbicidal activity | | |
|---|---|---|---|---|
| Compound | Dosage (g/ha) | barn-yardgrass | giant foxtail | annual bluegrass |
| Compound A | 20 | 4 | 3 | 0 |
| Glyphosate | 1000 | 2 | 3 | 2 |
| Compound A + glyphosate | 20 + 1000 | 8 | 8 | 8 |

TEST EXAMPLE 2

Plastic pots each having an area of 26.5×19 cm$^2$ and a depth of 7 cm were filled with upland soil, and then seeded with giant foxtail (*Setaria faberi*) and southern crabgrass (*Digitaria ciliaris*). These test plants were grown in a greenhouse for 23 days.

An emulsifiable concentrate of compound E, which had been obtained by well mixing 10 parts of compound E, 14 parts of polyoxyethylene styryl phenyl ether, 6 parts of calcium dodecylbenzenesulfonate, 35 parts of xylene, and 35 parts of cyclohexanone, a formulation product of glyphosate as described above, and a mixture of the emulsifiable concentrate of compound E and the formulation product of glyphosate were independently diluted in their prescribed amounts with water. Each dilution was uniformly sprayed over the test plants with a small sprayer. The same procedure was repeated for compound O. After the application, the test plants were grown in the greenhouse for 4 days, and the herbicidal activity was then examined.

The results are shown in Table 3.

TABLE 3

| Compound | Dosage (g/ha) | Herbicidal activity | |
|---|---|---|---|
| | | southern crabgrass | giant foxtail |
| Compound E | 20 | 3 | 4 |
| Compound O | 20 | 3 | 4 |
| Glyphosate | 500 | 1 | 0 |
| Compound E + glyphosate | 20 + 500 | 8 | 7 |
| Compound O + glyphosate | 20 + 500 | 8 | 7 |

TEST EXAMPLE 3

Cylindrical plastic pots each having a diameter of 17 cm and a depth of 14.5 cm were filled with upland soil, and then seeded with giant foxtail (*Setaria faberi*), barnyardgrass (*Echinochloa crus-galli*), and annual bluegrass (*Poa annua*). These test plants were grown in a greenhouse: giant foxtail for 42 days, and barnyardgrass and annual bluegrass for 31 days.

An emulsifiable concentrate of compound A, which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexanone, a formulation product of glufosinate-ammonium (trade name, Basta; Hoechst Japan Limited), and a mixture of the emulsifiable concentrate of compound A and the formulation product of glufosinate-ammonium were independently diluted in their prescribed amounts with water. Each dilution was uniformly sprayed over the test plants with a small sprayer. After the application, the test plants were grown in the greenhouse for 4 days, and the herbicidal activity was then examined.

The results are shown in Table 4.

TABLE 4

| Compound | Dosage (g/ha) | Herbicidal activity | | |
|---|---|---|---|---|
| | | barn-yardgrass | giant foxtail | annual bluegrass |
| Compound A | 20 | 4 | 3 | 0 |
| Glufosinate-ammonium | 400 | 2 | 2 | 2 |
| Compound A + glufosinate-ammonium | 20 + 400 | 8 | 9 | 8 |

TEST EXAMPLE 4

Plastic pots each having an area of 26.5×19 cm² and a depth of 7 cm were filled with upland soil, and then seeded with giant foxtail (*Setaria faberi*) and southern crabgrass (*Digitaria ciliaris*). These test plants was grown in a greenhouse for 23 days.

An emulsifiable concentrate of compound E, which had been obtained by well mixing 10 parts of compound E, 14 parts of polyoxyethylene styryl phenyl ether, 6 parts of calcium dodecylbenzenesulfonate, 35 parts of xylene, and 35 parts of cyclohexanone, a formulation product of glufosinate-ammonium as described above, and a mixture of the emulsifiable concentrate of compound E and the formulation product of glufosinate-ammonium were independently diluted in their prescribed amounts with water. Each dilution was uniformly sprayed over the test plants with a small sprayer. The same procedure was repeated for compound O. After the application, the test plants were grown in the greenhouse for 4 days, and the herbicidal activity was then examined.

The results are shown in Table 5.

TABLE 5

| Compound | Dosage (g/ha) | Herbicidal activity | |
|---|---|---|---|
| | | southern crabgrass | giant foxtail |
| Compound E | 20 | 3 | 4 |
| Compound O | 20 | 3 | 4 |
| Glufosinate-ammonium | 500 | 5 | 3 |
| Compound E + glufosinate-ammonium | 20 + 500 | 10 | 8 |
| Compound O + glufosinate-ammonium | 20 + 500 | 10 | 8 |

INDUSTRIAL APPLICABILITY

A wide variety of weeds in upland fields, particularly in corn fields and in soybean fields, can be effectively controlled by the present composition.

I claim:

1. A herbicidal composition for foliar treatment comprising as active ingredients,
   (a) a compound of the general formula:

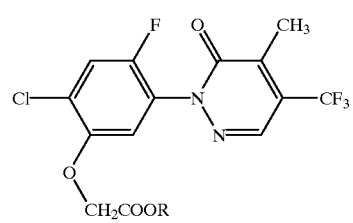

[1]

wherein R is $C_1$–$C_7$ alkyl, $C_5$–$C_6$ cycloalkyl, $C_2$–$C_6$ alkenyl, dimethylamino, or diethylamino; and
   (b) N-(phosphonomethyl)glycine (glyphosate) or a salt thereof, or ammonium DL-homoalanin-4-yl(methyl) phosphinate (glufosinate-ammonium).

2. The herbicidal composition according to claim 1, for control of weeds in corn fields.

3. The herbicidal composition according to claim 1, for control of weeds in soybean fields.

4. The herbicidal composition according to claim 1, wherein component (a) is compound in which R is $C_1$–$C_7$ alkyl, $C_5$–$C_6$ cycloalkyl, or $C_2$–$C_6$ alkenyl, and component (b) is glyphosate or a salt thereof.

5. The herbicidal composition for foliar treatment according to claim 4, wherein the weight ratio of component (a) to component (b) is 1:5 to 500.

6. The herbicidal composition according to claim 4 or 5, for control of weeds in corn fields.

7. The herbicidal composition according to claim 4 or 5, for control of weeds in soybean fields.

8. The herbicidal composition according to claim 1, wherein component (a) is compound in which R is dimethylamino or diethylamino, and component (b) is glyphosate or a salt thereof.

9. The herbicidal composition for foliar treatment according to claim 8, wherein the weight ratio of component (a) to component (b) is 1:5 to 500.

10. The herbicidal composition according to claim 8 or 9, for control of weeds in corn fields.

11. The herbicidal composition according to claim 8 or 9, for control of weeds in soybean fields.

12. The herbicidal composition according to claim 1, wherein component (a) is compound in which R is $C_1$–$C_7$ alkyl, $C_5$–$C_6$ cycloalkyl, or $C_2$–$C_6$ alkenyl, and component (b) is glufosinate-ammonium.

13. The herbicidal composition for foliar treatment according to claim 12, wherein the weight ratio of component (a) to component (b) is 1:2 to 200.

14. The herbicidal composition according to claim 12 or 13, for control of weeds in corn fields.

15. The herbicidal composition according to claim 12 or 13, for control of weeds in soybean fields.

16. The herbicidal composition according to claim 1, wherein component (a) is compound in which R is dimethylamino or diethylamino, and component (b) is glufosinate-ammonium.

17. The herbicidal composition for foliar treatment according to claim 16, wherein the weight ratio of component (a) to component (b) is 1:2 to 200.

18. The herbicidal composition according to claim 16 or 17, for control of weeds in corn fields.

19. The herbicidal composition according to claim 16 or 17, for control of weeds in soybean fields.

20. A weeding method comprising foliar treatment of weeds with an effective amount of a herbicidal composition containing as active ingredients, (a) a compound of the general formula:

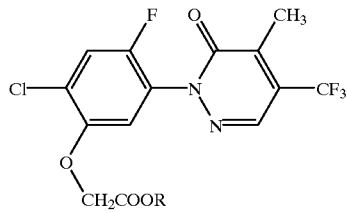

[1]

wherein R is $C_1$–$C_7$ alkyl, $C_5$–$C_6$ cycloalkyl, $C_2$–$C_6$ alkenyl, dimethylamino, or diethylamino; and (b) N-(phosphonomethyl)glycine (glyphosate) or a salt thereof, or ammonium DL-homoalanin-4-yl(methyl)phosphinate (glufosinate-ammonium).

21. The weeding method according to claim 20, wherein the herbicidal composition is applied to the weeds so that the total amount of component (a) and component (b) is 10 to 2000 g/ha.

22. The weeding method according to claim 20 or 21, wherein the herbicidal composition is applied to the weeds in corn fields.

23. The weeding method according to claim 20 or 21, wherein the herbicidal composition is applied to the weeds in soybean fields.

24. The weeding method according to claim 20, wherein component (a) is compound in which R is $C_1$–$C_7$ alkyl, $C_5$–$C_6$ cycloalkyl, or $C_2$–$C_6$ alkenyl, and component (b) is glyphosate or a salt thereof.

25. The weeding method according to claim 24, wherein the weight ratio of component (a) to component (b) is 1:5 to 500.

26. The weeding method according to claim 24 or 25, wherein the herbicidal composition is applied to the weeds so that the total amount of component (a) and component (b) is 10 to 2000 g/ha.

27. The weeding method according to claim 24 or 25 wherein the herbicidal composition is applied to the weeds in corn fields.

28. The weeding method according to claim 24 or 25 wherein the herbicidal composition is applied to the weeds in soybean fields.

29. The weeding method according to claim 20, wherein component (a) is compound in which R is dimethylamino or diethylamino, and component (b) is glyphosate or a salt thereof.

30. The weeding method according to claim 29, wherein the weight ratio of component (a) to component (b) is 1:5 to 500.

31. The weeding method according to claim 29 or 30, wherein the herbicidal composition is applied to the weeds so that the total amount of component (a) and component (b) is 10 to 2000 g/ha.

32. The weeding method according to claim 29 or 30, wherein the herbicidal composition is applied to the weeds in corn fields.

33. The weeding method according to claim 29 or 30, wherein the herbicidal composition is applied to the weeds in soybean fields.

34. The weeding method according to claim 20, wherein component (a) is compound in which R is $C_1$–$C_7$ alkyl, $C_5$–$C_6$ cycloalkyl, or $C_2$–$C_6$ alkenyl, and component (b) is glufosinate-ammonium.

35. The weeding method according to claim 34, wherein the weight ratio of component (a) to component (b) is 1:2 to 200.

36. The weeding method according to claim 34 or 35, wherein the herbicidal composition is applied to the weeds so that the total amount of component (a) and component (b) is 10 to 2000 g/ha.

37. The weeding method according to claim 34 or 35, wherein the herbicidal composition is applied to the weeds in corn fields.

38. The weeding method according to claim 34 or 35, wherein the herbicidal composition is applied to the weeds in soybean fields.

39. The weeding method according to claim 20, wherein component (a) is compound in which R is dimethylamino or diethylamino, and component (b) is glufosinate-ammonium.

40. The weeding method according to claim 39, wherein the weight ratio of component (a) to component (b) is 1:2 to 200.

41. The weeding method according to claim 39 or 40, wherein the herbicidal composition is applied to the weeds so that the total amount of component (a) and component (b) is 10 to 2000 g/ha.

42. The weeding method according to claim 39 or 40, wherein the herbicidal composition is applied to the weeds in corn fields.

43. The weeding method according to claim 39 or 40, wherein the herbicidal composition is applied to the weeds in soybean fields.

44. The weeding method according to claim 26, wherein the herbicidal composition is applied to the weeds in corn fields.

45. The weeding method according to claim 26, wherein the herbicidal composition is applied to the weeds in soybean fields.

46. The weeding method according to claim 31, wherein the herbicidal composition is applied to the weeds in corn fields.

47. The weeding method according to claim 31, wherein the herbicidal composition is applied to the weeds in soybean fields.

48. The weeding method according to claim 36, wherein the herbicidal composition is applied to the weeds in corn fields.

49. The weeding method according to claim 36, wherein the herbicidal composition is applied to the weeds in soybean fields.

50. The weeding method according to claim 41, wherein the herbicidal composition is applied to the weeds in corn fields.

51. The weeding method according to claim 41, wherein the herbicidal composition is applied to the weeds in soybean fields.

* * * * *